United States Patent [19]
Kubera et al.

[11] Patent Number: 5,972,661
[45] Date of Patent: Oct. 26, 1999

[54] MIXING SYSTEMS

[75] Inventors: Paul M. Kubera, Webster, N.Y.; John R. McWhirter, Boalsburg, Pa.; Bradley S. Dominik, San Diego, Calif.; Prakash G. Balan, State College, Pa.

[73] Assignees: Penn State Research Foundation, University Park, Pa.; General Signal Corporation, Rochester, N.Y.

[21] Appl. No.: 09/162,088

[22] Filed: Sep. 28, 1998

[51] Int. Cl.$^6$ ...................................................... C12P 19/06
[52] U.S. Cl. ............................... 435/104; 261/87; 261/93; 261/123; 366/292; 366/295; 366/296; 435/41; 435/266; 435/289.1; 435/295.1
[58] Field of Search ............................. 435/41, 104, 266, 435/289.1, 295.1

[56] References Cited

U.S. PATENT DOCUMENTS

| | | |
|---|---|---|
| 3,092,678 | 6/1963 | Braun . |
| 3,460,810 | 8/1969 | Mueller . |
| 3,962,042 | 6/1976 | Malick . |
| 3,966,542 | 6/1976 | Oldshue . |
| 4,207,275 | 6/1980 | Stanton . |
| 4,224,414 | 9/1980 | Vanderveen et al. . |
| 4,256,839 | 3/1981 | Solomons et al. . |
| 4,378,436 | 3/1983 | Heine et al. . |
| 4,403,868 | 9/1983 | Kupka . |
| 4,454,077 | 6/1984 | Litz . |
| 4,454,078 | 6/1984 | Englebrecht . |
| 4,545,945 | 10/1985 | Prave et al. . |
| 4,564,063 | 1/1986 | Tollar . |
| 4,703,007 | 10/1987 | Mulholland . |
| 4,717,669 | 1/1988 | Feres et al. . |
| 4,750,994 | 6/1988 | Schneider . |
| 4,904,601 | 2/1990 | Mano et al. . |
| 4,906,574 | 3/1990 | Erdei et al. . |
| 4,906,577 | 3/1990 | Armstrong et al. . |
| 4,919,849 | 4/1990 | Litz et al. . |
| 4,934,828 | 6/1990 | Janssen . |
| 5,004,571 | 4/1991 | Litz et al. . |
| 5,073,311 | 12/1991 | Nojima et al. . |
| 5,085,809 | 2/1992 | Stirling . |
| 5,244,603 | 9/1993 | Davis . |
| 5,248,613 | 9/1993 | Roubicek . |
| 5,314,076 | 5/1994 | La Place et al. . |
| 5,451,349 | 9/1995 | Kingsley . |
| 5,454,986 | 10/1995 | Lessen . |
| 5,503,220 | 4/1996 | Wood et al. . |
| 5,593,890 | 1/1997 | Flores-Cotera et al. . |

*Primary Examiner*—Herbert J. Lilling
*Attorney, Agent, or Firm*—Harris Beach & Wilcox, LLP

[57] ABSTRACT

A system for providing improved bulk liquid mixing and effective gas-liquid contacting for mass transfer of the gas to the liquid, especially a non-Newtonian liquid, the viscosity of which decreases when under shearing conditions (shear thinning), in an upright tank. A process, such as fermentation which produces commercial quantities of polysaccharides such as xanthan gum, may be carried out in the tank. An upright draft tube is mounted within the tank and has a lower end spaced from the tank bottom and an upper end spaced below the surface of the liquid in the tank. A plurality of mixing impellers in the draft tube are sufficiently close to each other to establish a field or pattern of agitation to cause shear thinning and upflow throughout the draft tube and which may produce turbulence at the liquid surface. A plurality of radially inwardly projecting, circumferentially spaced baffles extend from the draft tube and are proximate the mixing impellers to prevent swirling of the liquid within the draft tube. Gas may be sparged into the vessel in or adjacent to the lower end of the draft tube. A circulating co-current flow of gas and liquid, with intimate gas-liquid contact, is induced up through the draft tube and out the upper end of the draft tube so as to provide a high rate of mass transfer from the gas to the liquid. The flow including entrained gas turns down through the annular region between the tank wall and the draft tube for recirculation of the liquid and gas above the surface of the liquid, resulting in high gas holdup and gas-liquid contact in the downflow annular region and in the upflow draft tube region, without gas flooding of the impellers. The concentration of dissolved gas and the effectiveness of the system for gas-phase mass transfer is determined by reaeration of a test sample of the liquid. Additional surface aeration can be provided with a surface impeller having a plurality of blades with vertical portions and outwardly inclined portions, the vertical portions being inclined with respect to radial lines from the axis of rotation of the impeller.

5 Claims, 11 Drawing Sheets

MIXING SYSTEMS

The present invention relates to mixer systems, and particularly to systems (methods and apparatus) for the circulation and gas-liquid contacting of liquids in a tank, especially when such liquids have non-Newtonian, shear thinning viscosity characteristics. Good circulation and mixing of the liquid and intimate gas-liquid contacting facilitates mass transfer of a gaseous component into the liquid.

The invention is especially suitable for use in bio-reaction processes, such as fermentation by circulating slurries containing microbes and growth media, especially where the fermentation process increases the viscosity of the slurry. The present invention enables improved oxygenation and mixing of such liquids to promote the fermentation process. A fermentation process in which the invention finds particular application is a process for producing polysaccharides such as xanthan gum, and improves such process by enabling increased circulation and mixing of the solution and oxygenation thereof at high concentrations of xanthan gum which results in such high viscosities so as to preclude effective circulation and mixing thereof by conventional means, such that the value of the product of the fermentation, which is a function of the concentration of xanthan gum, is increased or produced in a shorter period of time.

Non-Newtonian liquids which can be effectively mixed and oxygenated with a mixing system embodying the invention have shear thinning characteristics, that is the viscosity of such liquids decreases significantly in the presence of shear. Regions in which shear is produced, in the attempt to reduce the viscosity of the liquid so as to enable it to be circulated, have in conventional systems been confined to the immediate vicinity of the impellers used to circulate the liquid. Such regions have sometimes been referred to as caverns of shear thinned liquid surrounding the impellers. The remaining liquid, for example in a tank in which the impellers are located, remains at high viscosity and thus does not circulate or mix to the extent required for effective gas transfer, and particularly oxygenation of the entire body of liquid in the tank. These non-mixed or non-circulating portions of the tank liquid are often referred to as "dead zones" and significantly reduce the overall effectiveness of the fermentation process.

It has been discovered in accordance with the invention that circulation of a substantial volume fraction of the liquid in the tank enables circulation of the entire body of liquid in the tank. In the case of shear thinning (non-Newtonian) liquids, a shear field or pattern of agitation effects circulation of the liquid when it is achieved within a substantial volume of the liquid in a tank. Shear fields or patterns which produce flow in a direction other than the direction of circulation, for example, a swirling flow, is inhibited in accordance with the invention. The flow through the substantial volume of liquid causes flow elsewhere throughout the tank thereby circulating the entire body of liquid to obtain good top to bottom turnover of the liquid in the tank. The introduction of gas into the circulating flow and the gasification thereof as may be required by the process, for example a fermentation process ongoing in the tank, is then achievable.

It has been proposed to use various expedients for enhancing mixing and circulation in a tank. However, these techniques have been unable to provide adequate circulation and mixing at flow rates sufficient to facilitate the process under the severe circulation and mixing conditions such as presented by many non-Newtonian, shear thinning liquids, especially in fermentation processes.

Accordingly it is an object of the invention to provide an improved mixing system which enables effective mixing and circulation of liquids under severe mixing conditions, especially those presented by non-Newtonian (shear thinning) liquids.

It is a still further object of the present invention to provide an improved system involving circulation of liquids and the gasification thereof which can be carried out effectively with high viscosity, shear thinning liquids.

It is a still further object of the present invention to provide improved impeller systems, which effect circulation of liquids in a tank, which are efficient in terms of the power required to produce a required flow in the tank.

It is a still further object of the present invention to provide an improved impeller which facilitates surface gasification by creating a spray of liquid above the surface of the liquid in the tank, such surface gasification being referred to herein as surface aeration, without limitation to the nature of the gas (whether air or oxygen or some other gas) at the surface of the liquid in the tank.

It is still a further object of the invention to provide a mixing environment that reduces the apparent viscosity of the solution and thereby increases the liquid phase mass transfer and thus increases the overall gas-liquid mass transfer.

It is a still further object of the present invention to provide an improved method of determining the efficiency of gasification which is referred to herein as mass transfer of the gas to the liquid in terms of an overall liquid phase mass transfer coefficient, $k_L a$, and particularly to a method for measurement of the oxygenation of the liquid by unsteady state reaeration so as to enable such measurements to be accurately made where standard dissolved oxygen probes and standard Winkler dissolved oxygen titration procedures are not useful because of the high viscosity and ineffective mixing of the bulk liquid phase and the opaqueness of the aerated liquid medium.

Briefly described, the present invention may be embodied in a mixer system disposed below the surface of the liquid in a tank (the surface being measured when the liquid is static, as when not being circulated) and utilizes a plurality of impellers spaced from each other along the axis of a stationary draft tube, around which axis the impellers are rotated. The draft tube provides coaxial regions inside and outside of the tube, with the diameter of the tube and its length being such that the tube occupies a substantial volume fraction of the liquid in the tank. The impellers include a plurality of impellers, and the impellers create a shear field or pattern of agitation and a pressure gradient to produce good circulation upwardly through the inside region and then downwardly through the outside region. The impellers provide agitation fields which are coupled to each other, and particularly which overlap. Swirling flow inside the draft tube is inhibited, for example, by baffles which project radially inwardly from the draft tube wall and axially between the impellers and preferably above and below the upper and lower most impellers.

Gas may be sparged (injected) into the flow entering the draft tube and/or at the liquid surface. In such event the gasification by entrainment of gas in the tank above the liquid surface may be enhanced by the use of a surface aeration impeller. Also the circulation at the top of the draft tube may be enhanced by a shroud which bridges the inner and outer regions.

The surface aeration impeller may be provided by a plurality of blades spaced circumferentially from each other and disposed at acute angles to radial lines from the axis of rotation of the impeller. The lower portions of the blades, which may extend below the surface, may be folded outwardly. The blades drive the liquid into a spray umbrella in a direction upwardly and outwardly away from the surface.

BRIEF DESCRIPTION OF THE DRAWINGS

The foregoing and other objects, features and advantages of the invention as well as presently preferred embodiments thereof and the best mode of carrying out the methods provided by the invention will become more apparent from the reading of the following description in connection with the accompanying drawings in which.

Figure 1:
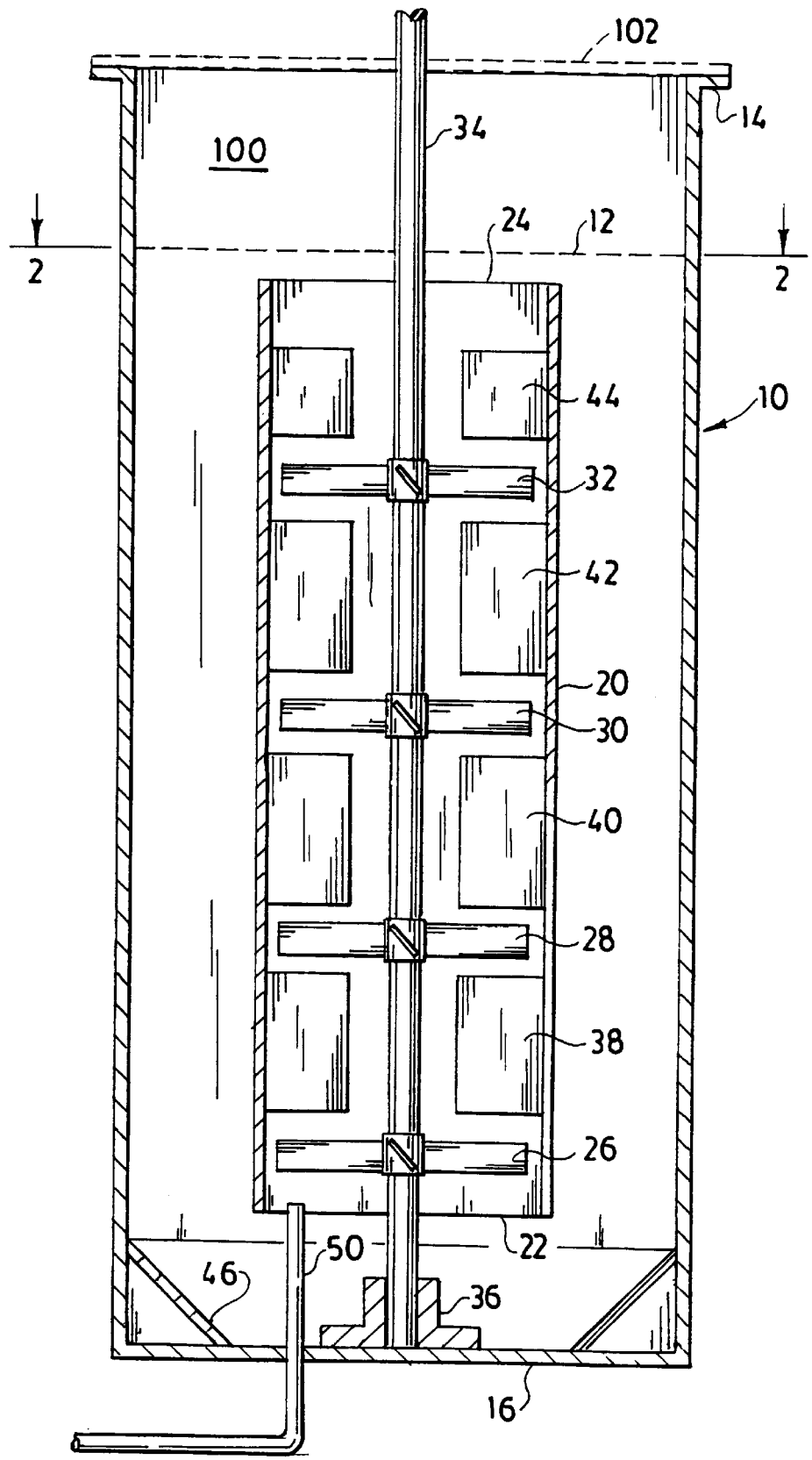
FIG. 1 is a diagrammatic, sectional front elevational view of a tank containing a mixing impeller system in accordance with the invention.
Figure 2:
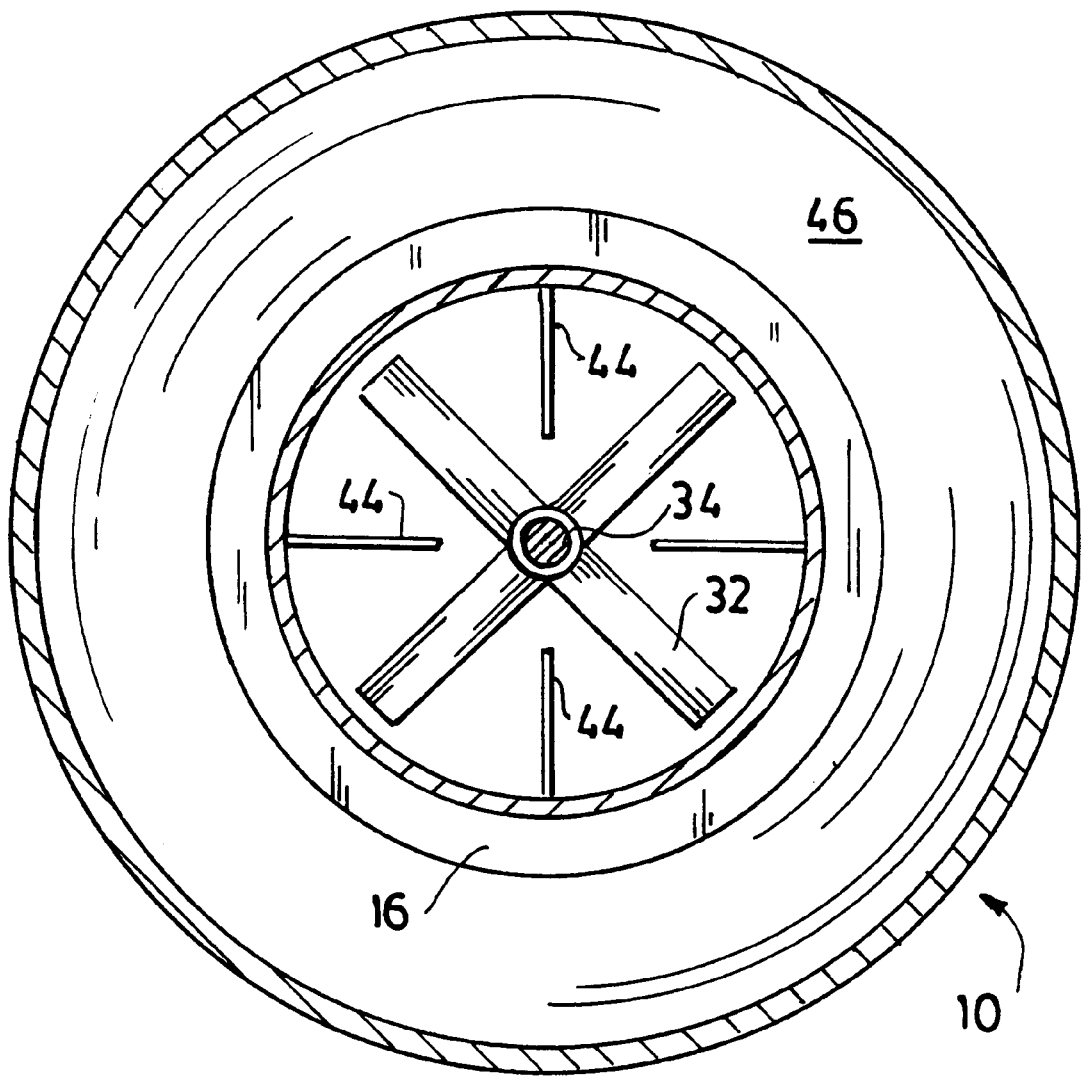
FIG. 2 is a sectional view taken along the line 2—2 in FIG. 1 when viewed in the direction of the arrows.

Referring first to FIGS. 1 and 2, there is shown a mixing system which has been found practical and effective for use in processes for mixing and circulating and gasifying non-Newtonian liquids and liquid slurries. The system of FIG. 1 has been found especially suitable for improving the mixing and mass transfer rate in bioreaction processes, including fermentation, and particularly a process for producing xanthan gum solutions. Presented hereinafter are examples illustrating a mixing and oxygenation process using air as the gaseous oxygenation medium on a solution simulating a high concentration (three to four percent by weight) solution of xanthan gum. The ability to effectively mix and oxygenate such solutions and produce the products of fermentation at concentrations having enhanced commercial value is an important feature of this invention.

Non-Newtonian liquids are characterized by having a variable viscosity which is a function of the applied shear force. Newtonian liquids such as water and mineral oil have a constant viscosity. The viscosity of non-Newtonian liquids changes when in a shear field, that is where the liquid is subject to a changing shear rate (1/sec). Xanthan gum solutions in the three percent by weight range are a commercially relevant non-Newtonian solution in that their viscosity, when at rest, is of the order of 10,000 cp, (centipoise) (for example 10,000 to 30,000 cp) and 100 cp when subject to a high shear rate. All viscosity values referred to herein are determined on a Brookfield viscometer.

In gasification processes, such as the oxygenation of the broth in fermentation, it is desirable to continue gasification until the oxygen can no longer be transferred at a high enough rate to sustain the microorganisms in the fermentation broth. When approaching this condition in polysaccharide fermentations, the viscosity increases to a point that the rate of oxygenation and circulation of the broth can no longer supply the oxygen demand of the microorganisms. When this condition is reached, the fermentation cannot be continued. The mixing systems provided by the present invention maintain non-Newtonian liquids, such as xanthan gum solutions, at low viscosity by maintaining a large fraction of the solution under high shear rates, even under these conditions (high three percent or greater xanthan gum concentrations) so that continued effective oxygen transfer and mixing can be maintained. Thus, as the process proceeds from startup, the low viscosity initial condition (100 to 200 cp in xanthan gum solutions) is maintained because of the high shear rate in a significant volume fraction of the liquid being mixed and circulated. Gasification can then proceed to higher xanthan gum concentrations in the liquid a large fraction of which is maintained at sufficiently low viscosity to enable good circulation and oxygen transfer throughout the entire volume of liquid in the fermenter.

As shown in FIGS. 1 and 2, the liquid is in a tank 10 and has a liquid level 12 below the upper end or rim 14 of the tank when the liquid in the tank is static (that is not being circulated or turned over) between the surface 12 and the bottom 16 of the tank. The tank 10 may be generally cylindrical and the tank walls arranged vertically upright. A cylindrical draft tube 20 is mounted preferably centrally of the tank. Then the axis of the draft tube 20 is coincident with the axis of the tank 10 when the tank is cylindrical. The diameter of the draft tube and its length is such that the internal volume defined by the tube 20 is a substantial part, at least 25% and preferably 50% of the volume of the liquid in the tank 10. There is clearance between the bottom 16 of the tank and the lower end 22 of the draft tube. The upper end 24 of the draft tube is in the vicinity of the static liquid surface 12. A plurality of mixing impellers 26, 28, 30 and 32 are attached to, and driven by, a common shaft 34. The upper end of the shaft may be connected to a drive motor via a gear box (not shown) and the lower end of the shaft 34, may be journaled in a steady bearing 36. The impellers are all of the same type, namely so-called pitched blade turbines (PBT), having a plurality of four blades circumferentially spaced about the axis of rotation, the axis being the axis of the shaft 34 and the blades are disposed at 45° to that axis. Such PBT impellers are available from the Lightnin Unit of General Signal Corporation, Rochester, N.Y. 14611, USA, as their Model A200. Alternatively, other axial flow impellers may be used, such as airfoil-type blades (sometimes called hydrofoil blades). Such air foil axial flow impellers may, for example, be the A-315, which is presently available from the Lightnin Unit and which is described in Weetman, U.S. Pat. No. 4,896,971. Other air foil impellers which may be suitable are described in U.S. Pat. No. 4,468,130, also issued to Weetman.

The mixing system in the draft tube also includes sets 38, 40, 42 and 44 of four vertical baffles which are 90° displaced circumferentially about the axis of the shaft 34, as shown in other FIGS. discussed hereinafter, between the impellers.

Other sets of baffles may be located above, and, if desired below, the upper and lower most impellers 32 and 26. In other words, two pairs of baffles are contained in each set and the pairs are 180° displaced with respect to each other (See FIG. 2). The impellers 26–32, with the aide of the sets of baffles 38–44, produce a field or pattern of agitation which provide a high level of shear in the liquid in the draft tube. Thus, in the case of non-Newtonian, shear thinning liquids, the viscosity of the liquid in the draft tube is maintained sufficiently low so that it enhances mass transfer and promotes improved circulation in the tank. The circulation, which has been found to produce the most effective mixing, is in the upward direction inside the draft tube to regions at the ends of the draft tube 32 and 24 where the flow changes direction, so that the flow is downward in the annular region between the draft tube 20 and the sidewall of the tank 10.

The annular region between the draft tube wall 20 and the sidewall of the tank 10 is a region of low shear and hence high effective viscosity for shear thinning liquids. Nonetheless, good uniform flow with no stagnant regions is maintained down through this high viscosity annular region by virtue of the high flow rate generated up through the low viscosity draft tube zone. Thus, the annular region between the draft tube wall 20 and the sidewall of the tank 10 has a relatively high average axial fluid velocity and the liquid is quickly recirculated into the high shear, low viscosity draft tube region.

The relative sizing of the draft tube diameter and impellers and their locations in the draft tube are related by the flow rate so that the requisite circulation and mixing may be obtained. Then the rate of flow and volume contained in the draft tube and the volume of the tube are sufficient to establish the axial flow between the tube and wall of the tank over a broad range of viscosities up to and including viscosities of the order of $10^4$ cp (Brookfield).

To prevent stagnant zones at the corner formed by the sidewall and the bottom 16 of the tank 10, it is desirable to install an annular plate or ring 46 which defines a fillet to smooth the flow past the corner. Alternatively, the plate may be convexly, inwardly curved so as to provide a generally circular contour for the fillet 46. In order to gasify the liquid, a sparge pipe 50 directs the gas into the lower end of the draft tube, preferably in proximity to the tips (the radially outward most or peripheral ends) of the blades of the lower most impeller 26. The introduction of the gas is known as sparging. The term aeration is generally used to connote the introduction of any gas including atmospheric air or oxygen enriched air. Substantially pure (90 to 95%) oxygen may also be used. Gas dispersion or gas incorporation into the liquid also occurs due to turbulence at the liquid surface 12 where there is gas-liquid contacting and entrainment of the gas into the liquid so that it recirculates downwardly through the outer annular region. Because of the high shear rate in the draft tube, the liquid is at low viscosity and enables the gas from the sparge pipe 50 to be broken up into fine bubbles which present a large total gas-liquid interfacial area to facilitate mass transfer. The effectiveness of oxygen mass transfer may be measured in terms of the overall liquid phase mass transfer coefficient ($K_L a$).

In order to provide the high shear conditions (high shear rate sufficient to reduce the viscosity of the liquid in the tank so that it can circulate readily and uniformly), the impellers 26, 28, 30 and 32 are spaced sufficiently close to each other so that the field or pattern of their flow overlaps. When the overlapping fields of flow is created, the agitation produces not only axial, but also significant radial force on the fluid.

The sets 38, 40, 42 and 44 of baffles inhibit this radial component, which produces a swirling flow, so that the flow upward through the draft tube is substantially axial. The baffles preferably project radially inwardly by distances sufficient to inhibit the radial flow of the liquid. Preferably, the height of the baffles is such that the spacing between the upper and lower edges of the baffles and the adjoining impellers is the minimum to provide a practical running clearance for the impellers 26–32.

The following parameters have been found to provide suitable conditions for effective liquid circulation and mixing and mass transfer and oxygenation. It will be appreciated that the specific values which are selected, depend upon the material (liquid, liquid slurry or other medium) being circulated and aerated. The characteristics are generally listed in their order of criticality. It is a feature of the invention to provide a mixing system wherein each of these parameters is used so as to secure the benefits of efficient liquid mixing and circulation and effective gas-liquid contacting (mass transfer), especially in bio-reaction processes. The parameters are as follows:

1. The ratio of the draft tube diameter to the tank diameter is between about 0.35 and 0.75, with a ratio of about 2/3 (.667) being presently preferred.
2. The ratio of impeller diameter to draft tube diameter is from about 0.5 to 0.96. All of the impellers 26–32 are generally of the same diameter between the tips of the blades. If impellers of different diameter are used, the largest diameter impeller is used in selecting this parameter, i.e. the ratio of the impeller diameter to the draft tube diameter.
3. Impeller vertical spacing, that is the distance between the mean height of the impeller, as measured between the leading and trailing edges of the blades thereof, is between 0.70 and 1.30 of the diameter of the largest of two adjacent impellers. In other words, where the adjacent impellers have the same diameter, they may be from about 0.70 to 1.30 of an impeller diameter apart. Where the adjacent impellers have different diameters, the largest diameter is used to determine spacing in the range 0.70 to 1.30 of the larger of the two adjacent impeller diameters. Preferably, the impellers are spaced apart so that their midlines are separate by about 1.0 impeller diameter.
4. The ratio of the radial width of the vertical baffles inside the draft tube to the diameter of the draft tube is preferably in the range of about 0.1 to 0.4. A ratio of about 0.33 of radial width to draft tube diameter is presently preferred. The height of the baffles in the vertical direction should approach the impellers, and preferably be adjacent thereto, allowing only sufficient spacing for rotation of the impellers without interference.
5. There preferably are two to four baffles in each set of baffles adjoining the impellers.
6. The upper end of the draft tube may be submerged from the liquid surface up to about 0.3 of the diameter of the draft tube. In cases where a surface aeration impeller is used or where a diverting shroud is used, as will be described hereinafter in connection with FIGS. 8 to 11, the submergence of the draft tube may be sufficient to enable insertion of the surface aerator and/or the flow diverter at the top of the draft tube. However, the volume of the liquid in the tank occupied by the draft tube should remain substantial and be at least about 0.25 of the volume of the liquid in the tank (between the bottom of the tank, the liquid level and within the sidewalls of the tank). The uppermost impeller should also be less than about one impeller diameter from the surface of the liquid in the tank. The placement of the uppermost impeller is selected which engenders good surface turbulence and further gas-liquid contacting for enhancing the gas transfer rate and the mass transfer coefficient of the system.

7. The off-bottom clearance of the bottom of the draft tube is preferably from about 0.3 to about 0.7 of the draft tube diameter. The preferred parameter is 0.5 of the draft tube diameter for the spacing or off-bottom clearance of the bottom or lower end of the draft tube from the bottom of the tank.

Figure 3:
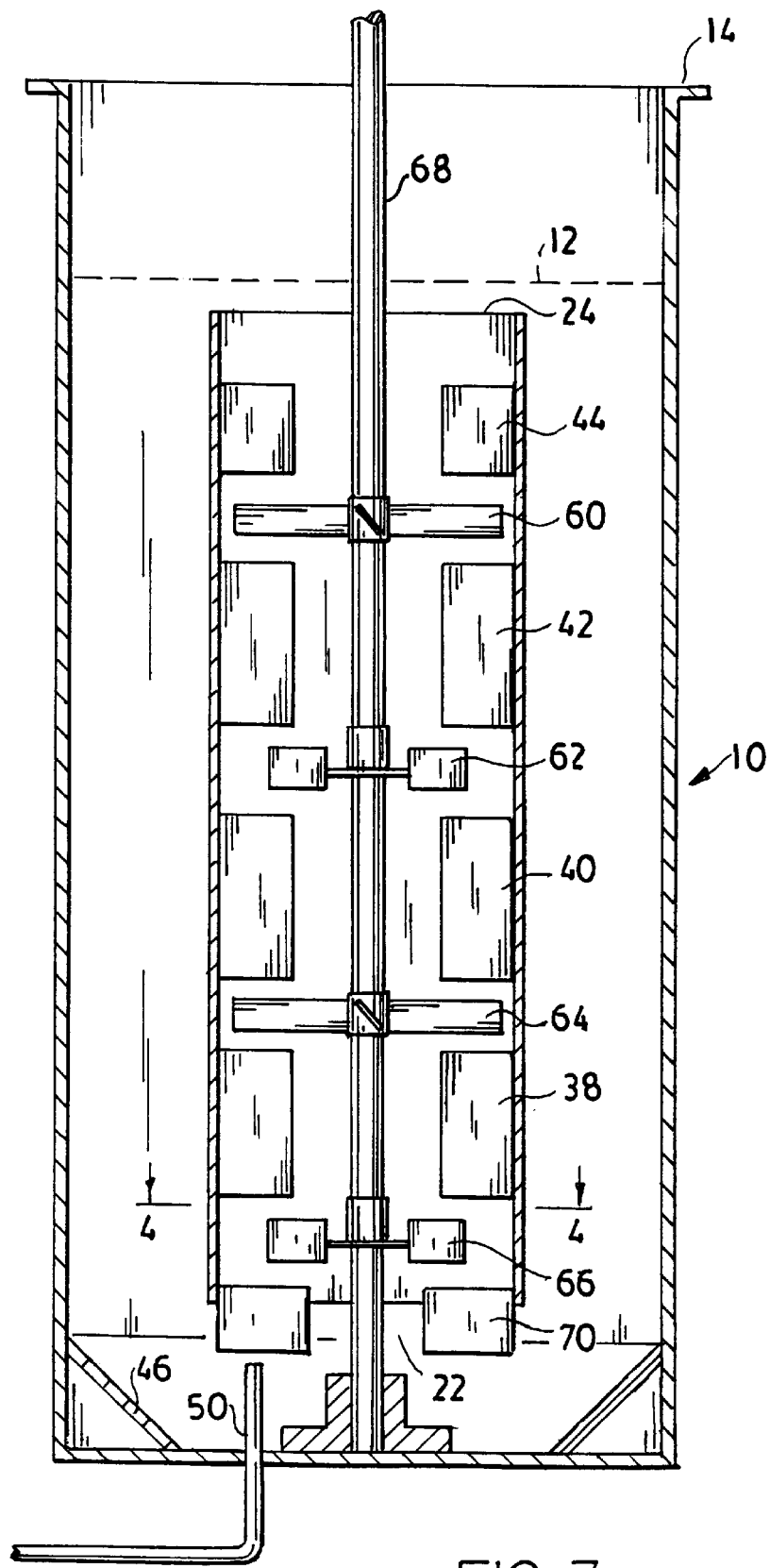
FIG. 3 is a view similar to FIG. 1 showing another embodiment of an impeller system in accordance with the invention.
Figure 4:
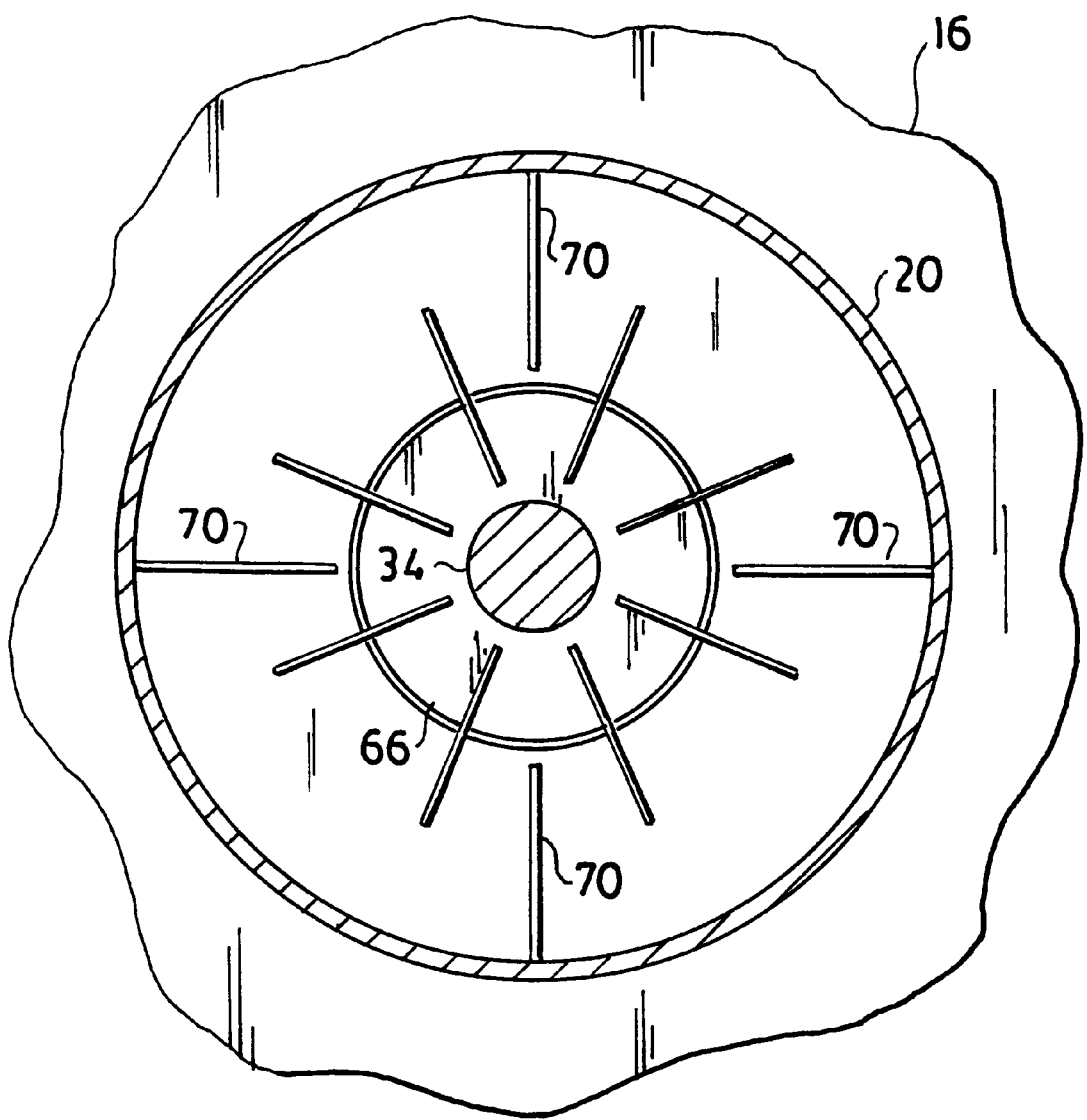
FIG. 4 is a sectional view taken along the line 4—4 in FIG. 3.

Referring to FIGS. 3 and 4, there is shown an impeller system having four impellers 60, 62, 64 and 66. There are two axial flow impellers 60 and 64 and two radial flow impellers 62 and 66 which are disposed alternately along the axis of rotation (which is the axis of a shaft 68 which is common to all of the impellers). The axial flow impellers may be PBT's or airfoil blade impellers, such as discussed in connection with FIGS. 1 and 2. The radial flow impellers 62 and 66 may be so-called Rushton turbines, such as R-100 class radial flow impellers, which are presently available from the Lightnin Unit of General Signal Corporation. Information as to the design of radial flow impellers may be found in Englebrecht and Weetman, U.S. Pat. No. 4,454,078 and Stanton, U.S. Pat. No. 4,207,275.

FIG. 3 also illustrates a lowermost set 70 of vertical baffles which may extend outwardly from the lower end 22 of the draft tube, or the lower edge of the baffle may be coincident with the lower end of the draft tube.

Gas is sparged into the lower end of the draft tube. The radial and axial flow impellers are closely coupled so that their agitation patterns and shear fields overlap thereby enabling good axial upward circulation of the liquid through the draft tube and recirculation through the annulus between the draft tube and the sidewall of the tank.

Figure 5:
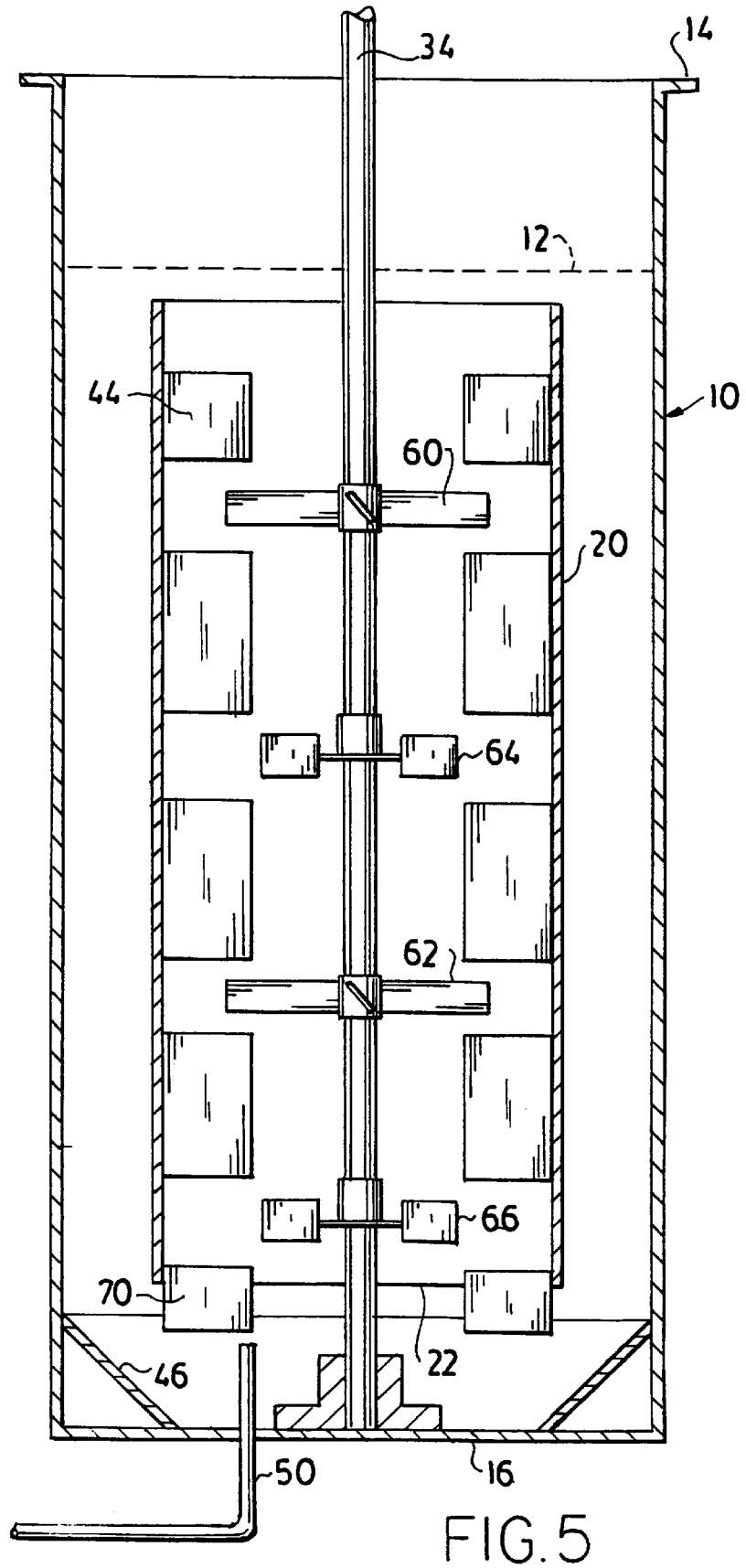
FIG. 5 is a view similar to FIG. 1 showing another embodiment of the invention.

The system shown in FIG. 5 is similar to the system shown in FIG. 3 except that the draft tube occupies a larger volume fraction of the liquid in the tank and the baffles extend radially inward a lesser distance in respect to the diameter of the larger impellers (the axial flow impellers 60 and 64 ) than in the case of the system shown in FIGS. 3 and 4.

The use of alternate axial and radial flow impellers provides for adequate mixing, circulation and gasification, and affords ample circulation rates (for example ½ foot per second flow), even in the annulus around the draft tubes, so as to produce good liquid mixing and top to bottom turnover and ample mass transfer of the gas to the liquid and dispersion and solution of the gas into the liquid. To the extent that the parts shown in FIGS. 3, 4, and 5 are similar to those shown in FIGS. 1 and 2, like reference numerals are used.

Figure 6:
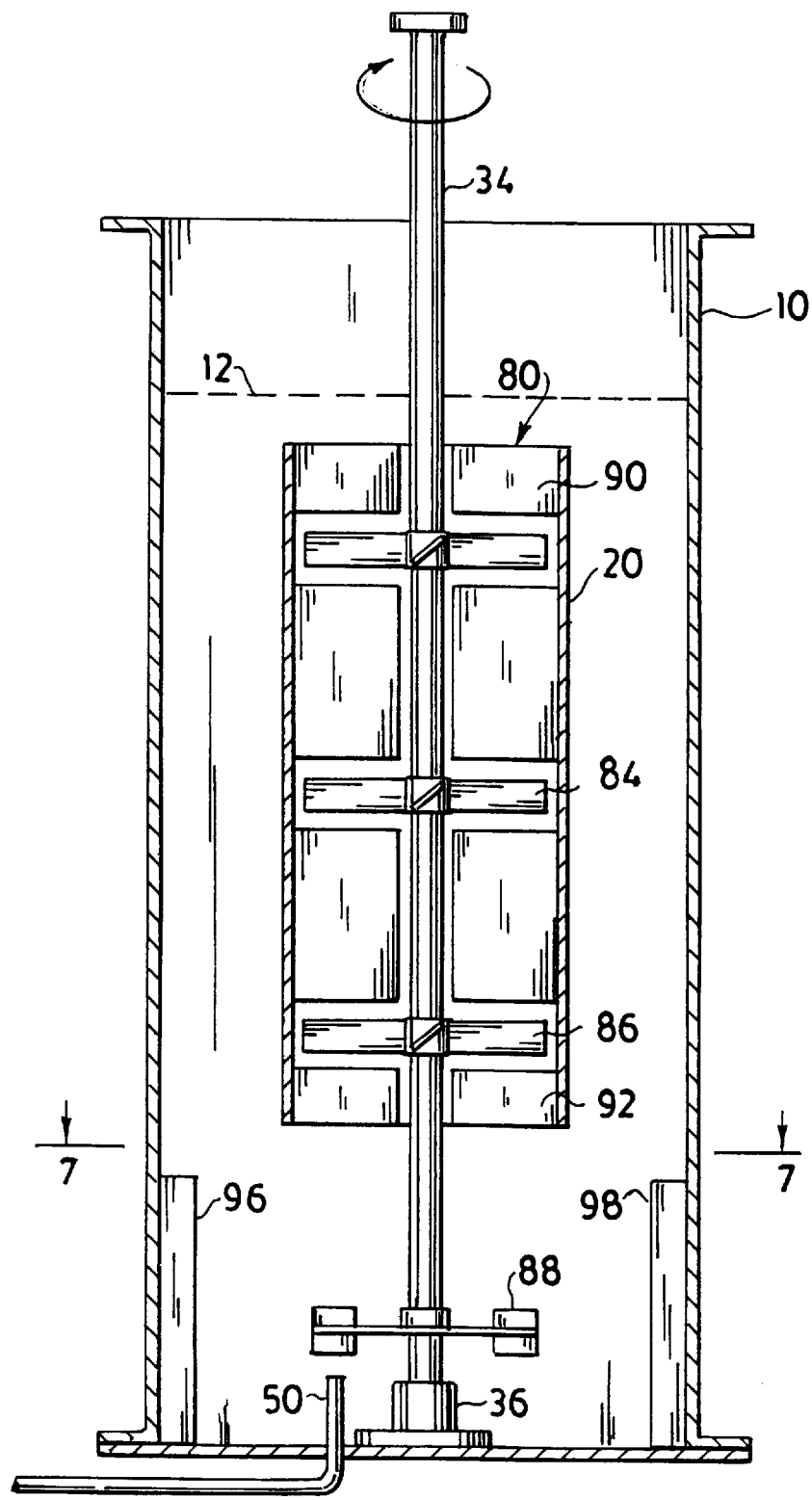
FIG. 6 is a view, similar to FIG. 1, showing still another embodiment of the invention.
Figure 7:
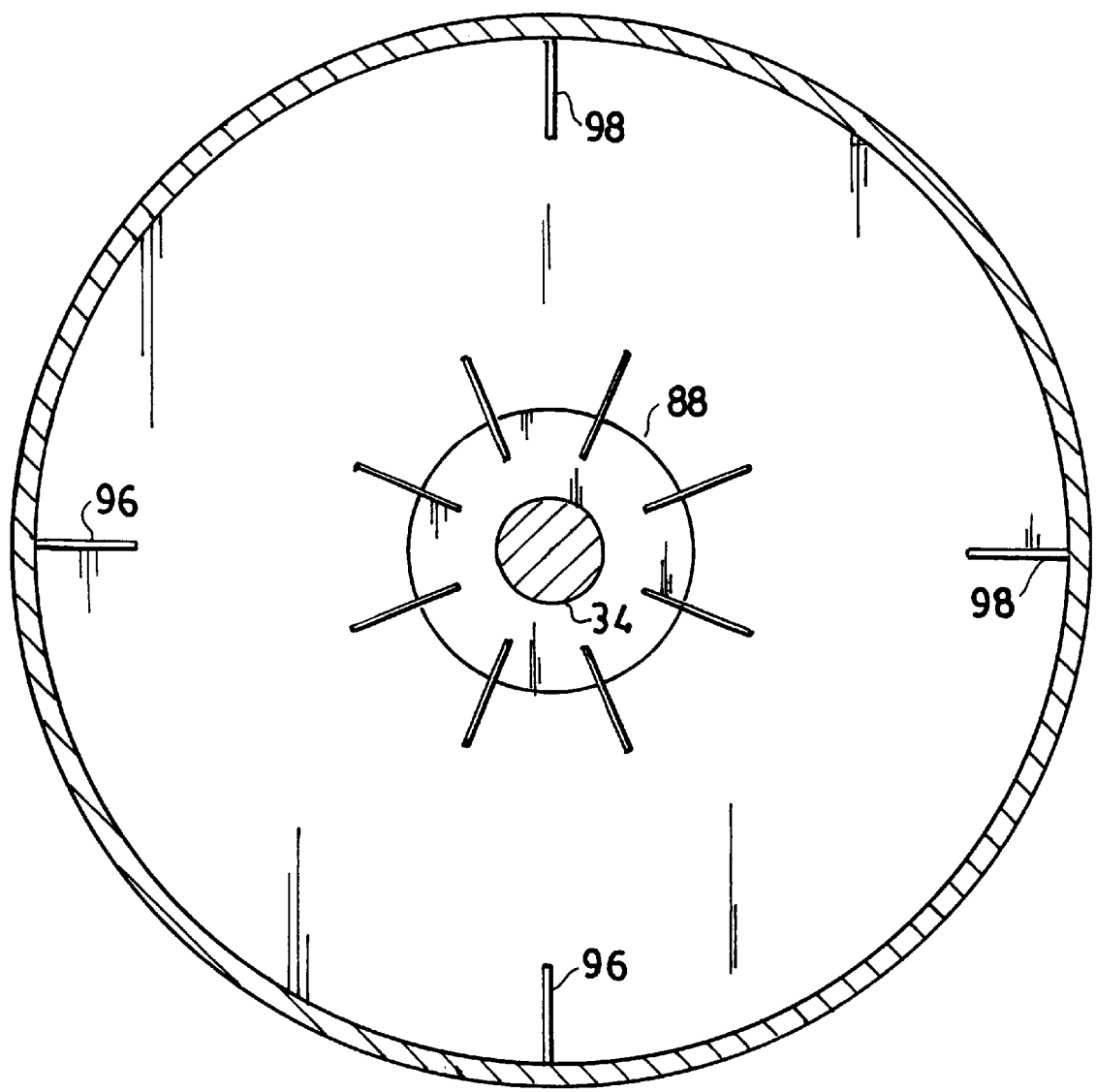
FIG. 7 is a sectional view taken along the line 7—7 in FIG. 6 when viewed in the direction of the arrows.

Referring to FIGS. 6 and 7, there is shown a mixing system 80 in the tank 10 having three axial flow impellers 82, 84 and 86 inside the draft tube 20 and a radial flow impeller 88 on the shaft 34 common to all the impellers. The radial flow impeller 88 is located below the draft tube in the region where the liquid flow turns upwardly into the draft tube. In the case of the impellers in the draft tube, the baffles, especially in the set of baffles at the uppermost and lowermost end of the draft tubes (sets 90 and 92 in FIG. 6), reduces swirl, as well as promoting the circulation upwardly through the draft tube and then down into the annulus between the sidewalls of the tank and the draft tube 20. The radial flow impeller has a power number (the ratio of the power in horse power which is needed to drive the impeller to the product of the cube of the speed of the impeller and the diameter to the fifth power of the impeller) which is much higher than and preferably about equal to the sum of power numbers of the impellers in the draft tube; thus the radial flow impeller 88 draws at least as much power as all of the three impellers 82, 84 and 86 in the draft tube. The agitation field from the radial flow impeller 88 extends up to the lower end of the draft tube and facilitates the creation of the agitation pattern and shear field in a sufficient volume of the tank to promote complete turnover or circulation (top to bottom mixing) of the liquid in the tank 10. Also the radial flow impeller facilitates effective dispersion of the gas from the sparge pipe into the mixing system. To inhibit swirl in the mixing pattern of the radial flow impeller 88, a plurality (at least two pairs) of vertical baffles 96 and 98 are disposed along the sidewalls of the tank 10 and extend at least half the distance from the bottom of the tank to the bottom of the draft tube for typical liquid media which are being mixed, circulated and aerated.

In the event that gasification is done with a gas other than air and especially in all fermentation processes, it is desirable that the overhead gas space (the distance between the rim 14 of the tank and the liquid level 12, shown at 100 in FIG. 1) be sealed by a cover 102. For example, when oxygen is used as the gas for aeration purposes, the overhead is desirably sealed. The oxygen may be introduced by a conduit which enters the overhead 100 via the sidewall of the tank.

Figure 8:
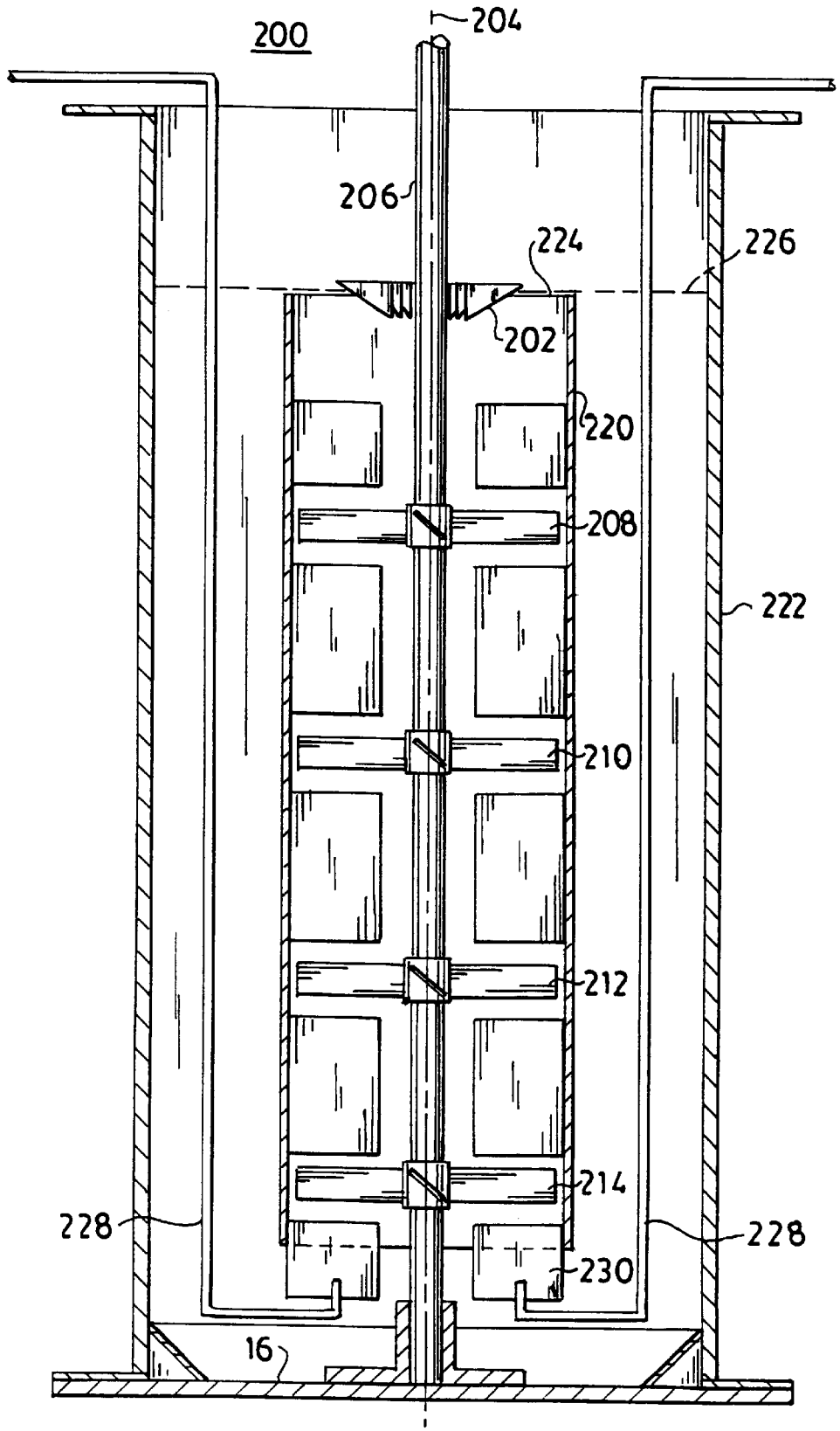
FIG. 8 is a view, similar to FIG. 1 showing still another embodiment of the invention.

Referring to FIG. 8, there is shown another embodiment of the invention utilizing a mixing system 200, having a radial flow surface aeration impeller 202 with blades circumferentially spaced about the axis of rotation 204 of the common drive shaft 206 of the impeller 202 and four axial flow 45° PBT impellers 208, 210, 212 and 214. The surface aeration impeller 202 may suitably be a Lightnin Model R-335 impeller and provides additional gas-liquid interfacial area by affording a spray umbrella, thereby entraining additional air back into the surface liquid which is recirculated down the angular region between the draft tube 220 and the sidewalls of the tank 222. The surface aerator 202 also provides additional upward liquid pumping action through the draft tube 220. Where a surface aerator is used, the upper end 224 of the draft tube may be coincident with the surface 226 of the liquid(the static liquid level in the tank).

In the system shown in FIG. 8, separate sparge pipes 228 are provided which extend downwardly along the side wall of the tank to the lowermost set 230 of baffles. The sparge pipes hook upwardly into the draft tube so as to facilitate introduction of the gas directly into the draft tube. It is a feature of the invention to provide sparging either into the draft tube or into the overhead gas space or both. When substantially pure oxygen is used, it is introduced into the overhead space, into the sparge pipes, such as the array of pipes 228, or both into the overhead and into the array of pipes.

Figure 9:
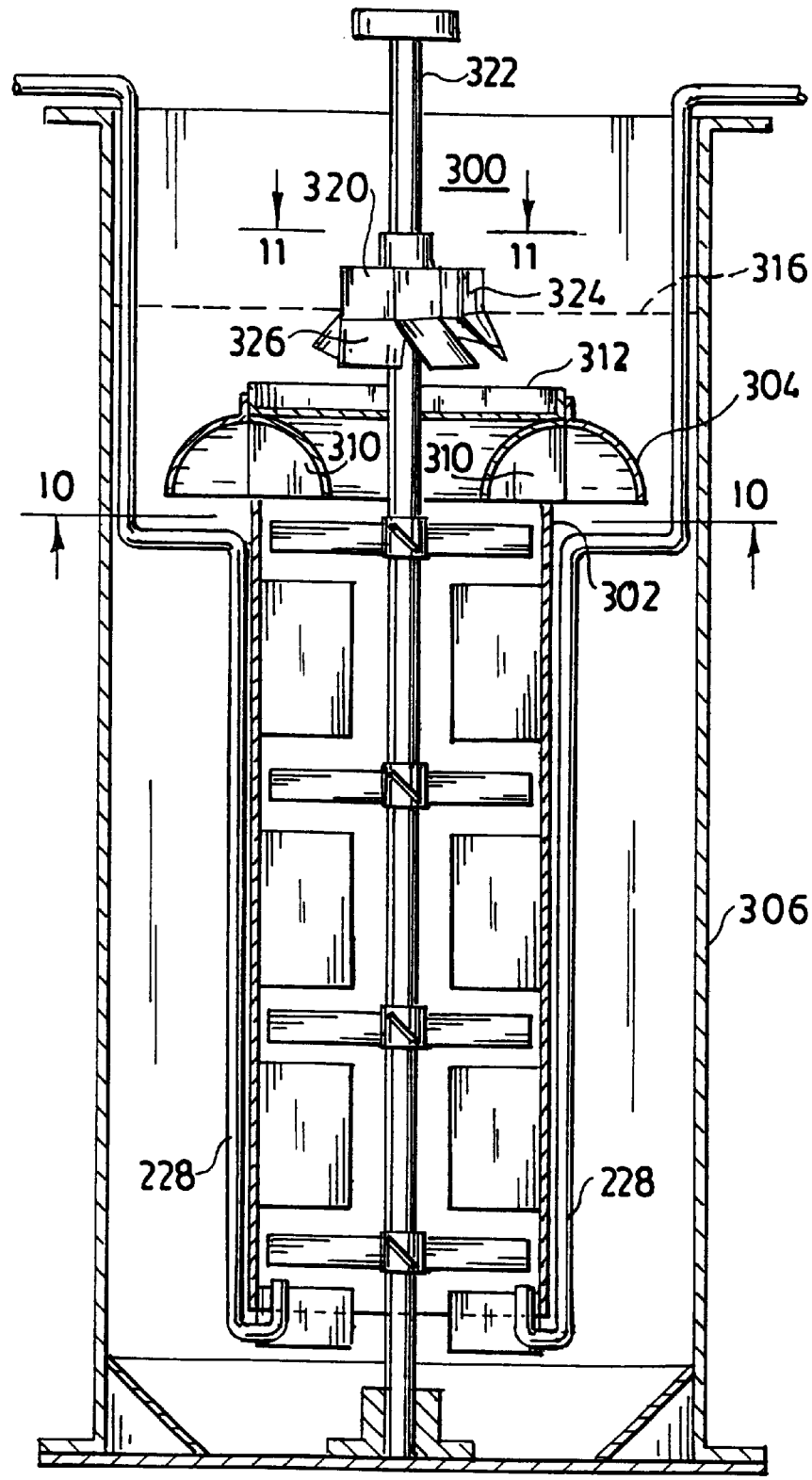
FIG. 9 is a view, similar to FIG. 1, showing still another embodiment of the invention.
Figure 10:
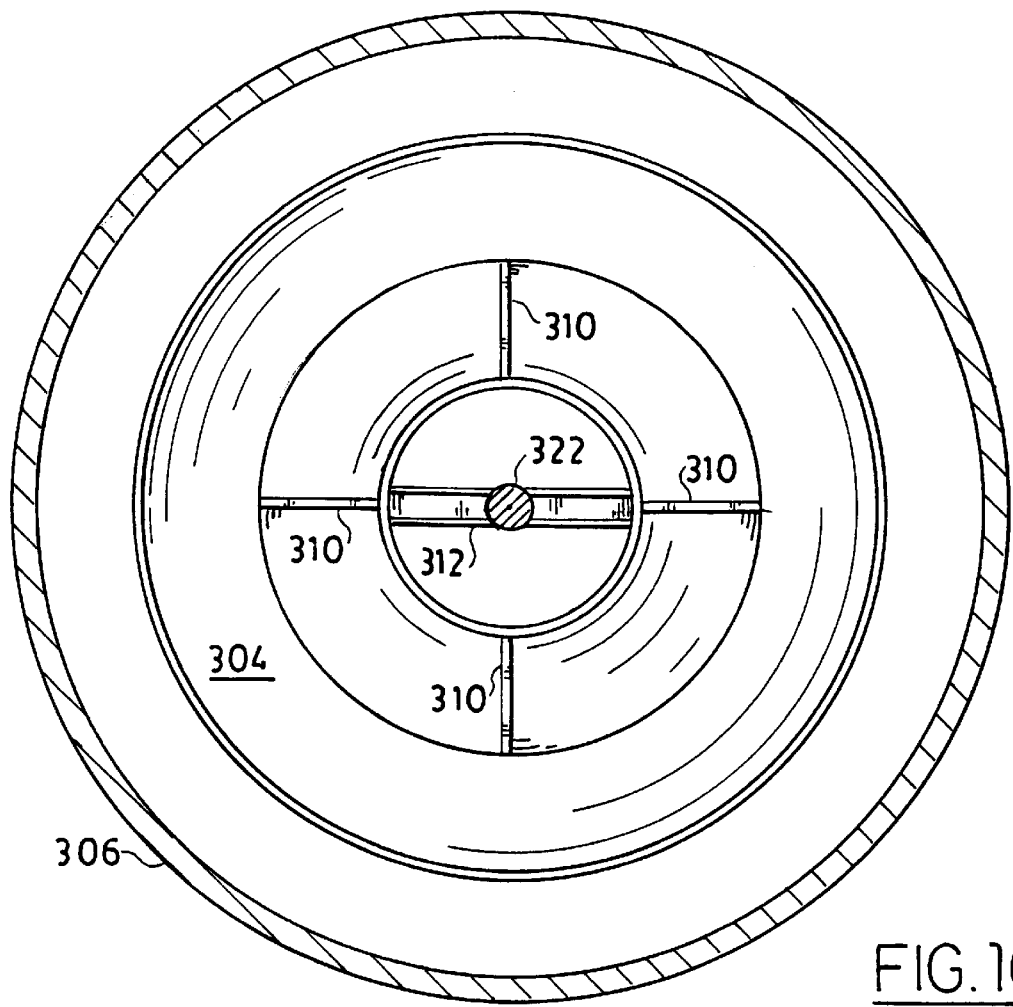
FIG. 10 is a sectional view along the line 10—10 in FIG. 9 when viewed in the direction of the arrows.
Figure 11:
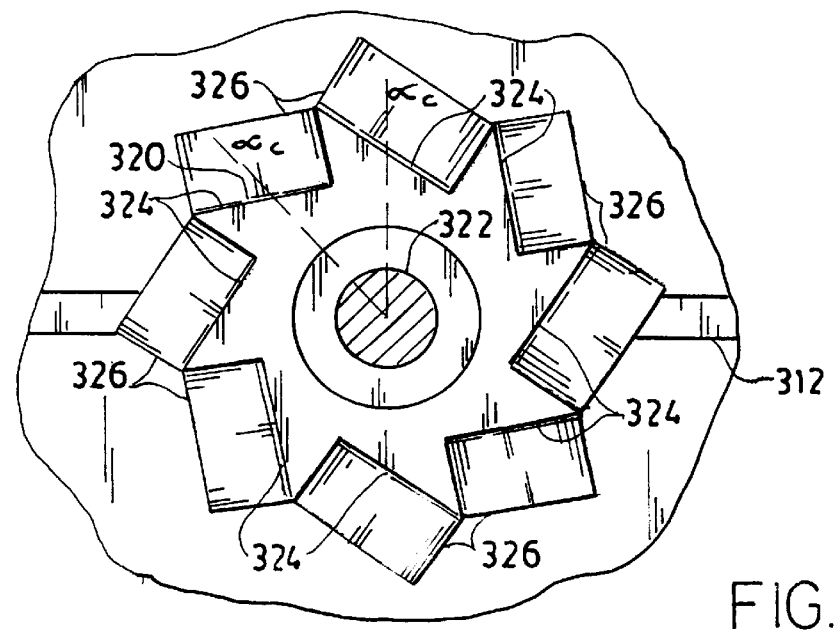
FIG. 11 is a sectional view along the line 11—11 in FIG. 9.

Referring to FIGS. 9, 10 and 11, there is shown an impeller system 300 having, in addition to an arrangement of impellers and baffles in a draft tube 302, similar to the arrangement of impellers 208, 210, 212 and 214 and their associated baffles, a shroud 304 to facilitate the diversion of the upward flow of liquid out of the draft tube into the annular region between the draft tube 302 and the sidewalls of the tank 306. This shroud may be a hemi-toroidal shell which has radial baffles at least one and preferably two pairs of baffles 310, 180° apart are used to inhibit radial flow and short circuiting of the flow back into the draft tube. These baffles extend radially inwardly from approximately the draft tube to the inner periphery of the shroud 304. The shroud 304 may be stiffened by a rod or angle iron 312. The connection to the draft tube may be by welds along the lower edges of the baffles 310 and the upper edge of the draft tube.

Extending through the static surface level 316 of the liquid in the tank 306, is an improved surface aeration impeller. This impeller has a plurality of vertically extending blades 320. Each blade is disposed at an angle (alpha— ) of approximately 30° to a successive, circumferentially spaced radial line around the axis of the impeller (the axis of the common shaft 322). These blades have vertical portions 324 at the upward ends thereof. The blades 320 also have, preferably extending below the liquid surface 316, portions 326 which are bent outwardly and define obtuse angles of approximately 120 to 135 degrees with respect to the vertical portions 324 thereof. The blades act as scoops to provide ample flow to the spray umbrella liquid from the surface aerator. The spray falls back over the shroud 304 into the annular region between the sidewalls of the tank 306 and the draft tube 302, thereby further facilitating the entrainment of gas from the head space above the liquid and providing a larger mass transfer coefficient, $K_L a$. The embodiment shown in FIGS. 9–11 may be preferable when high purity oxygen is used as the gas in the process carried out in the tank 306.

Figure 12:
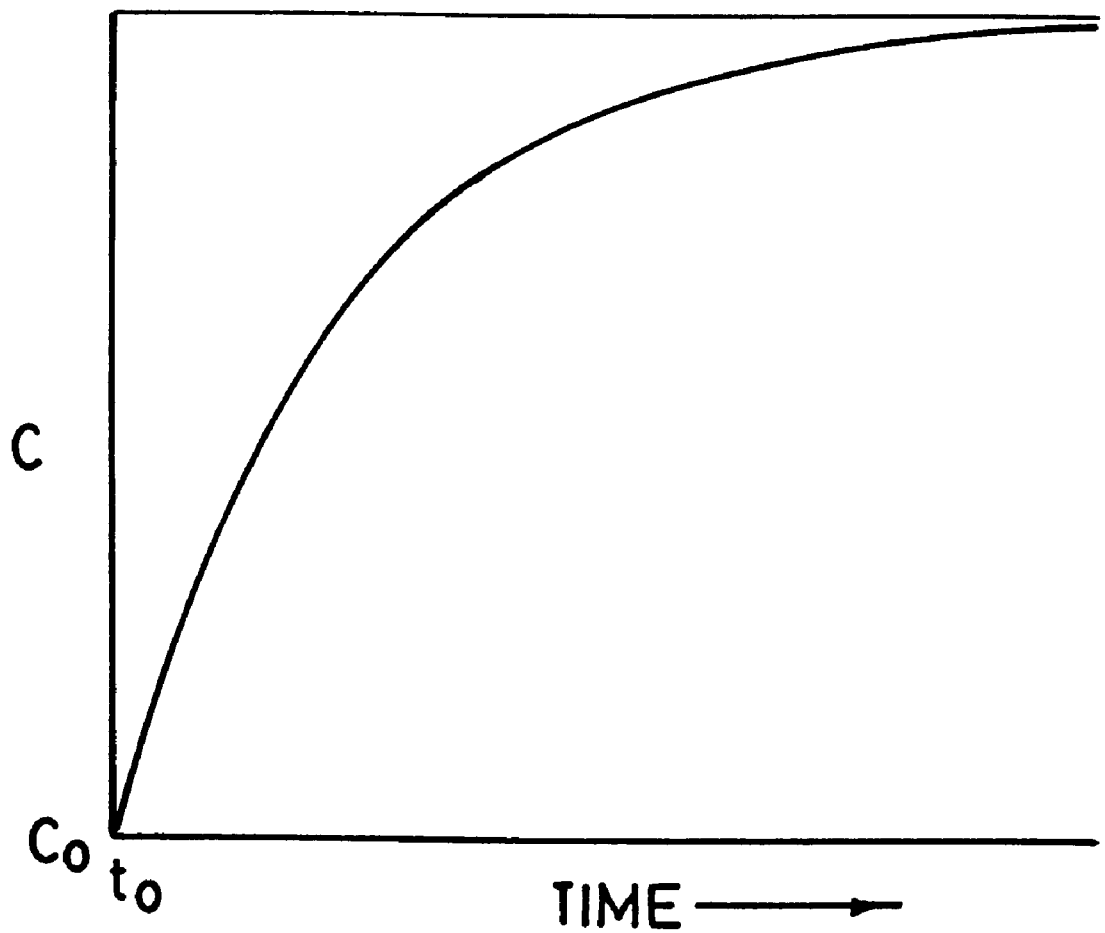
FIG. 12 is plot showing the changes in concentration of oxygen in a body of liquid, as a function of time, which has been oxygenated in a system such as shown in FIG. 1, and which plot is useful in deriving the mass transfer coefficient, $K_L a$, resulting from oxygenation of the body of liquid.

Referring to FIG. 12, there is shown a curve of dissolved oxygen, D.O., concentration measurements with time which is useful in determining the overall liquid phase mass transfer coefficient, $K_L a$. This mass transfer coefficient may be determined by means of an unsteady state reaeration test which uses dissolved oxygen concentration measurements with time from dissolved oxygen probes in the solution or by direct liquid sample titration. However, accurately determining the D.O. concentration measurements with time for high viscosity, opaque media such as xanthan gum solutions is extremely difficult. The accurate use of the unsteady state reaeration test procedure also requires good liquid mixing in the overall bulk liquid phase with no dead zones. Also regions of high flow are required where accurate calibration and use of D.O. probes can be achieved. The present invention provides an effective liquid mixing and circulation system which satisfies all of these requirements for accurate use of the unsteady state reaeration test procedure. Conventional liquid mixing systems cannot be effectively evaluated using the unsteady state test procedure for high viscosity, shear thinning fluids because of the poor level of bulk liquid mixing and turnover in the tank.

The unsteady state reaeration test is carried out by first making up a batch of the xanthan gum solution by mixing and aerating in the actual mixing and aeration system under test. This may be done for several hours so that there is assurance that the equilibrium dissolved oxygen level has been reached. Then, a test sample is extracted from the batch and the equilibrium dissolved oxygen content is measured using a modified Winkler dissolved oxygen titration procedure specifically adapted for high viscosity opaque solutions. The dissolved oxygen content at saturation is then used to calibrate the dissolved oxygen probes for the equilibrium-dissolved oxygen level (milligrams per liter of dissolved oxygen) in solution.

After the above D.O. probe calibration procedure is completed, the tank liquid is stripped of dissolved oxygen by bubbling a non-reacting gas, for example, nitrogen, through the batch in the tank. This may be done in the mixing system by replacing air or oxygen as the aerating gas with nitrogen. Measurements were made with the dissolved oxygen probe to show that the dissolved oxygen has been stripped from the liquid solution. This stripping may take 10 to 15 minutes. Then, reaeration with air or other oxygen containing gas is carried out until oxygen saturation is reached in the bulk liquid phase. Measurements are made of D.O. concentration, during reaeration, at successive periods of time. Then the curve, FIG. 12 is plotted. $t_o$ is the start of reaeration and $C_o$ is the initial D.O. concentration.

The oxygen transfer rate (OTR) at any point in time is the slope of the curve in FIG. 12 or $dC/dt$. The slope of the curve is also defined as being equal to $K_L a (C^*-C)$, where $C^*$ is equal to the equilibrium D.O. level, for example, from a sample taken from the middle of the tank. The solution of the resulting differential equation is equal to $C=C^*-(C^*-C_o) \exp[-(K_L a)]$. A statistical solution of the equation for the D.O. concentration versus time profile provides an overall lumped parameter $K_L a$ for the oxygen mass transfer process. This mass transfer coefficient, $K_L a$, is a measure of the effectiveness of the aeration in the mixing process and is used in the examples presented below to demonstrate the effectiveness of the process for different process conditions and parameters.

In examples 1 through 5, a system such as shown in FIGS. 1 and 2 is used where the impellers are 17 inch diameter PBT's. A four pipe gas sparge system such as shown in FIG. 8, rather than a single pipe sparge 50, was used. The liquid which was tested in the examples was a solution simulating a xanthan gum fermentation broth containing three to four percent by weight xanthan gum. The simulating solution was a solution of two percent by weight xanthan gum and 0.5M(molar) sodium sulfate, in water. The mass transfer coefficients given in the examples as the overall tank volume liquid phase mass transfer coefficient were measured using the unsteady state reaeration technique as specifically developed for directly and accurately measuring the liquid phase mass transfer coefficient for xanthan gum solutions as discussed above.

EXAMPLE 1

| | |
|---|---|
| Draft Tube Diameter | 18" |
| Tank Diameter | 36" |
| Liquid Level | 72" |
| Tank Height | 84" |
| Power Input | 23.6 HP/kgal |
| Gas sparge rate | 0.5 vvm |
| Liquid flow rate up through draft tube and down through annular region. | 3/2 liters/sec. |
| Overall tank liquid turnover time | 3.9 sec |
| Overall tank volume liquid phase mass transfer coefficient ($k_L a$) | 18.9 sec$^{-1}$ |

EXAMPLE 2

| | |
|---|---|
| Draft Tube Diameter | 24" |
| Tank Diameter | 36" |
| Liquid Level | 72" |
| Tank Height | 84" |
| Power Input | 23.6 HP/kgal |
| Gas sparge rate | 0.5 vvm |

-continued

| | |
|---|---|
| Liquid flow rate up through draft tube and down through annular region. | 5/6 liters/sec. |
| Overall tank liquid turnover time | 2.3 sec |
| Overall tank volume liquid phase mass transfer coefficient ($k_L a$) | 16.5 hr$^{-1}$ |

EXAMPLE 3

| | |
|---|---|
| Draft Tube Diameter | 18" |
| Tank Diameter | 36" |
| Liquid Level | 72" |
| Tank Height | 84" |
| Power Input | 23.6 HP/kgal |
| Gas sparge rate | 0.1 vvm |
| Liquid flow rate up through draft tube and down through annular region. | 444 liters/sec. |
| Overall tank liquid turnover time | 2.7 sec |
| Overall tank volume liquid phase mass transfer coefficient ($k_L a$) | 10.3 hr$^{-1}$ |

EXAMPLE 4

| | |
|---|---|
| Draft Tube Diameter | 24" |
| Tank Diameter | 36" |
| Liquid Level | 72" |
| Tank Height | 84" |
| Power Input | 23.6 HP/kgal |
| Gas sparge rate | 0.1 vvm |
| Liquid flow rate up through draft tube and down through annular region. | 456 liters/sec. |
| Overall tank liquid turnover time | 2.3 sec |
| Overall tank volume liquid phase mass transfer coefficient ($k_L a$) | 9.2 hr$^{-1}$ |

EXAMPLE 5

| | |
|---|---|
| Draft Tube Diameter | 18" |
| Tank Diameter | 36" |
| Liquid Level | 72" |
| Tank Height | 84" |
| Power Input | 15.75 HP/kgal |
| Gas sparge rate | 0.5 vvm |
| Liquid flow rate up through draft tube and down through annular region. | 240 liters/sec. |
| Overall tank liquid turnover time | 5.1 sec |
| Overall tank volume liquid phase mass transfer coefficient ($k_L a$) | 16.5 hr$^{-1}$ |

EXAMPLE 6

| | |
|---|---|
| Draft Tube Diameter | 24" |
| Tank Diameter | 36" |
| Liquid Level | 72" |
| Power Input | 15.75 HP/kgal |
| Gas sparge rate | 0.5 vvm |
| Liquid flow rate up through draft tube and down through annular region. | 276 liters/sec. |
| Overall tank liquid turnover time | 4.4 sec |
| Overall mass transfer coefficient ($k_L a$) | 12.5 hr$^{-1}$ |

In addition to the performance data included in the above examples, the new mixer system designs have no dead zones anywhere within the entire tank system bulk liquid phase and also achieve very effective gas dispersion throughout the tank. The average bubble size escaping from the liquid surface is in the range of ¼" to ½" in diameter as compared to 8" to 12" for conventional design systems. Also the mechanical stability of the entire mixer and tank system is greatly improved with essentially no violation or erratic movement of the mixer and tank system.

From the foregoing description, it will be apparent that there has been provided improved mixer systems which are especially adapted for providing effective liquid mixing and gas-liquid contacting and improved mass transfer for non-Newtonian, shear thinning solutions. Variations and modifications in the herein described systems, within the scope of the invention, will undoubtedly suggest themselves to those skilled in the art. Accordingly, the foregoing description should be taken as illustrative and not in a limiting sense.

We claim:

1. The method of providing bio-reaction in a tank which comprises the steps of introducing a slurry of a bacteria containing liquid and a growth medium into the tank, which slurry increases in viscosity as the bio-reaction proceeds, circulating said slurry upwardly and downwardly in inner and outer coaxial regions of said tank, said inner region occupying at least about twenty-five percent of the volume of said tank which contains said slurry, with the aide of a draft tube which separates said regions, said circulating step including the step of shearing said liquid throughout said inner region, and said shearing step comprising producing axial flow in said inner region while inhibiting swirl therein.

2. The method according to claim 1 further comprising the step of introducing gas selected from the group consisting of air, oxygen enriched air and substantially pure oxygen into said tank, said introducing step being carried out by self gasification, sparging of said gas into said inner region or both by sparging and self gasification.

3. The method according to claim 1 further comprising the step of spraying said liquid at said surface between said inner and outer regions with the aide of a surface aeration impeller located at the surface above said inner region.

4. The method according to claim 1 further comprising the step of producing radial flow of said liquid between the bottom of said draft tube and the bottom of said tank and sparging said gas into said radial flow.

5. The method according to claim 1 further comprising the step of impelling said liquid in said inner region radially and axially in alternate successive portions of said inner region with the aide of impellers which produce principally radial flow in said alternate successive regions.

* * * * *